United States Patent [19]
Uytterhoeven et al.

[11] Patent Number: 4,727,214
[45] Date of Patent: Feb. 23, 1988

[54] PROCESS FOR OBTAINING ETHYLENE FROM ETHANOL

[75] Inventors: Jan B. Uytterhoeven, Louvain; Julia M. Jacobs, Malle; Paul J. J. Tastenhoye, Tervueren; Pierre A. Jacobs, Gooik, all of Belgium

[73] Assignee: De Belgische Statt-L'Etat Belge, Brussels, Belgium

[21] Appl. No.: 8,728

[22] Filed: Jan. 30, 1987

[30] Foreign Application Priority Data

Jan. 30, 1986 [LU] Luxembourg ............................ 86284

[51] Int. Cl.$^4$ ............................................... C07C 1/00
[52] U.S. Cl. ................................................... 585/640
[58] Field of Search .......................................... 585/640

[56] References Cited

U.S. PATENT DOCUMENTS 3,240,697  3/1966  Miale et al. ........................ 585/640
4,481,177 11/1984  Valyocsik ............................ 502/77
4,638,106  1/1987  Pieters et al. ....................... 585/640

FOREIGN PATENT DOCUMENTS 0088495  9/1983  European Pat. Off. ............ 585/640

Primary Examiner—Curtis R. Davis
Attorney, Agent, or Firm—Sughrue, Mion, Zinn, Macpeak, and Seas

[57] ABSTRACT

This invention relates to a process for obtaining ethylene from anhydrous or aqueous ethanol by means of a catalyst of the crystalline aluminosilicate zeolite type of natural or synthetic origin.

9 Claims, No Drawings

PROCESS FOR OBTAINING ETHYLENE FROM ETHANOL

According to the present invention, for converting anhydrous or aqueous ethanol into ethylene, at least one catalyst of the crystalline zeolite type is used, said catalyst having, on the one hand, channels or pores formed by cycles or rings of oxygen atoms having 8 and/or 10 elements or members and, on the other hand, an atomic Si/Al ratio of less than about 20, this catalyst being used under such temperature conditions that it has a carbon selectivity for ethylene of about 100% by weight and has a rate of conversion of about 100% of ethanol into ethylene.

THE PRIOR ART

The electrovalence of the aluminum in the crystalline structure of the zeolites is balanced by the presence of an equivalent number of cations in the anionic position of the crystalline network. The cations are selected among the elements of the Ia, Ib, IIa, IIb, IIIa, IIIb, IVa, IVb, Va, VIb, VIIb and VIII groups of the Mendeljev table. Examples of cations are the alkaline metals, the alkaline-earth metals and the lanthanides. These elements must have a suitable physical size and a configuration to diffuse into the intracrystalline passages of the zeolite structure.

It is known, namely from the European patent application No. 85201301.0, to use catalysts of the crystalline aluminosilicate zeolite type containing a silicate of a metal $M_1$, having a valence of 3 and a tetrahedral coordination and containing possibly another charge compensating metal $M_2$, these catalysts having a metal $M_1$ content such that the molar ratio $(M_1-M_2/n)/(Si+M_1)$ (where n is the valence of said other metal) in percents is at most equal to about 1.5, for obtaining substantially pure ethylene, as the only hydrocarbon, from pure ethanol or from aqueous, even very diluted, solutions of ethanol, the ethanol conversion ratio being of almost 100%.

This invention is based on the discovery that a class of zeolites comprising numerous materials, some of which are natural materials, are able to convert, under suitable conditions, ethanol into ethylene not only with interesting yields, but also with a carbon selectivity for ethylene of about 100% by weight.

The structure of the zeolites can be defined as a tridimensional network of tetrahedra of $SiO_4$ and $AlO_4$ linked to each other by sharing all four oxygen atoms. According to the rule of Löwenstein, the following restriction exists in respect of the mutual arrangement of the $SiO_4$ and $AlO_4$ tetrahedra: two tetrahedra of $AlO_4$ cannot share oxygen atoms or, in a zeolite network, two $AlO_4$ tetrahedra cannot be next to each other.

This network, the geometry of which varies from one zeolite to the other, defines a system of cavities and/or pores, the size of which is variable from one zeolite to the other, but which are uniform for a given zeolite. These cavities are connected together by windows, by pores or by other cavities. These pores are either parallel and give therefore a monodimensional porosity or intersect in two or in the three dimensions and give them a bi- or tridimensional porosity. These cavities contain water molecules or ions having a large movement freedom. Said cavities or pores are formed by 8, 10 and/or 12 membered rings of oxygen atoms with openings of variable sizes expressed in Angströms (Å).

The zeolites may be distinguished from one another by their chemical composition and, more especially and precisely, but their X-ray diffraction pattern.

Minor modifications, in respect of the interplanar spacing and the intensities which can be seen on some diagrams, are caused by the amount of residual water in the pores or channels, to the replacement of some cations by others or to variations of the silica/alumina ratio, but these modifications do not express a structural variation of the zeolite.

A determined size of the pores allows, for a given zeolite, to absorb or reject determined molecules.

BRIEF DESCRIPTION OF THE INVENTION

It has now been found that catalysts of a zeolite class defined by precise parameters not only allow the conversion of anhydrous or aqueous ethanol into ethylene with a conversion rate of about 100% and a carbon selectivity for ethylene of about 100%, but also have a remarkable stability in terms of time on stream.

According to the present invention, for converting anhydrous or aqueous ethanol into ethylene, at least one catalyst of the crystalline zeolite type is used, said catalyst having, on the one hand, channels or pores formed by cycles or rings of oxygen atoms having 8 and/or 10 elements or members and, on the other hand, an atomic Si/Al ratio of less than about 20, this catalyst being used under such temperature conditions that it has a carbon selectivity for ethylene of about 100% by weight and has a rate of conversion of about 100% of ethanol into ethylene.

It has been found that the zeolites having pore openings formed by oxygen atom rings or cycles of more than 10 elements, for example those having pore openings formed by oxygen atom rings of 12 elements or members and/or those having an atomic Si/Al ratio of more than 20, have a poor stability as a function of time, even if a conversion rate of about 100% and an carbon selectivity for ethylene of about 100% by weight is observed, when said catalysts are used for dehydrating ethanol into ethylene.

A large number of crystalline aluminosilicate zeolites have the two above defined characteristic parameters and may be used as catalysts in the process or method according to this invention.

Some of these catalysts, namely those naturally occuring, may require a treatment after their extraction, so as to increase their stability. These natural occuring materials may be submitted to an ion exchange and/or to a treatment at a high temperature or to a treatment by means of an acid or a base or to a combination of these treatments.

The aluminosilicate zeolites which are found in nature and which meet, after possible treatment, the two above defined parameters are, inter alia, the following: ferrierite, heulandite, clinoptilolite, stilbite, erionite, chabazite, levinyte.

According to a feature of the invention, it is possible to use a mixture of natural zeolites, one of which has pores or channels formed by rings of oxygen atom having 8 and/or 10 elements or members and has a Si/Al atomic ratio of less than 20.

As synthetic zeolites, which may be used in accordance with the invention, since they have the two above defined critical parameters, the following may be cited:

on the one hand, those which correspond to natural zeolites, for example ferrierite, chabazite, erionite; on the other hand, those which are not known in nature, such as, for example, ZSM-47 (ZSM-6), T and ZSM-22 zeolites and the like.

These synthetic zeolites are described in patents or publications.

The following patents and publication describe the preparation of suitable synthetic zeolites:

U.S. Pat. No. 4,187,283 for zeolite ZSM-47 (ZSM-6);
U.S. Pat. No. 2,950,952 for zeolite T;
European Pat. No. 0 102716 for zeolite ZSM-22;
European Pat. No. 0 012473 for synthetic ferrierite;
British Pat. No. 574,911 for synthetic chabazite;
article of Hawkins D. B. (Clays and Clay Minerals, vol. 29, p. 331–340 (1981)) for clinoptilolite.

It has to be noted that the structure of non natural zeolites, particularly ZSM-47 (ZSM-6) and T zeolites, has been characterized by hydroconversion of n-decane (J. A. Martens, M. Tielen, P. A. Jacobs, J. Weitkamp, Zeolites, 4, 98–107 (1984)).

As usual for most catalytic applications of the zeolites, it is preferred that at least a part of the cations initially present in the zeolite is removed by ion exchange. Such an ion exchange can replace the cations by hydrogen ions or by ions such as, for example ammonium ions which may be converted into hydrogen ions by a subsequent heat treatment.

The catalyst may be used in various manners in the method according to the invention. Thus, the catalyst may be used as a fixed bed, as a fluidized bed or as several beds of carried catalyst. The catalyst may be used with or without a binder and possibly as an extruded product.

Substantially pure ethylene can be obtained by the process according to the invention from anhydrous or aqueous ethanol, for example from industrial alcohol containing about 94% by weight of ethanol or from a fermentation mixture which may contain only about 4% by weight of ethanol.

The anhydrous or aqueous ethanol is contacted with the catalyst, in gaseous or vapour phase, possibly in the presence of an inert gas, such as nitrogen or helium. If desired, these gases may be recycled.

After the reaction, a mixture of water and of an organic phase is obtained. This organic phase can be easily separated from the aqueous phase by mere cooling, so that an organic phase consisting almost exclusively of ethylene is recovered.

The ethanol liquor used in the method according to the invention may be manufactured from biomass fermentation or synthesized from coal or petroleum synthesized syngas, which contains ethanol in anhydrous form or in a more or less concentrated form, before submitting said ethanol liquor to the catalytic method of converting ethanol into ethylene according to this invention. The method allows substantial energy savings, since the starting ethanol liquor may have a low ethanol content which may be almost quantitatively converted into ethylene, due to the remarkable selectivity of the catalysts according to this invention.

The temperature at which the catalyst is maintained for the conversion of ethanol into ethylene may vary within wide limits, namely between 400 K. and 800 K., preferably between about 500 K. and 700 K., this temperature being the maximum temperature reached in the catalyst bed.

Similarly, the flow rate of the ethanol liquor passed through the catalyst bed may also vary within wide limits. Thus, this flow rate, determined by the weight hourly space velocity (WHSV) which corresponds to the weight of ethanol contacted with the catalyst per weight of catalyst per hour and may vary between 0.05 and 10 hours$^{-1}$, preferably between 0.25 and 5.0 hours$^{-1}$.

The optimum values of the temperature of the catalyst bed and of the flow rate of the ethanol liquor can be easily determined by experiments, taking into account the ethanol content of the starting liquor and the particular type of catalyst used with this liquor, in order to obtain the desired results.

The method according to the invention may be carried out at pressures of the starting ethanol-containing liquor and of the inert gas possibly used as diluent comprised between 1 and 10 atmospheres, although it is preferred to work at atmospheric pressure.

The catalysts used in the process according to the invention are not subjected to degeneration and have a remarkably high thermic and hydrothermic stability. Even in the presence of noticeable amounts of water, the catalysts do not loss their catalytic activity or selectivity during a long time on stream.

EXAMPLES

The following examples illustrate the invention:

Example 1

Preparation of the hydrogen form of a ZEOLON 700 zeolite and use of this catalyst for converting ethanol into ethylene.

(a) Preparation:

The catalyst was prepared from a commercial zeolite: ZEOLON 700 (Norton, lot no. 92017).

X-ray diffraction analysis has shown that the product was ferrierite.

For ferrierite, the following typical unit cell composition is given by W. M. Meier and D. H. Olson ("Atlas of Zeolite Structure Types" published by the Structure Commission of the International Zeolite Association, printed by Juris Druck+Verlag AG, Zurich, Switzerland, 1978, p. 39):

$$Na_2Mg_2Al_6Si_{30}O_{72} \cdot 8H_2O.$$

ZEOLON 700 was calcined at 823 K. during 12 hours in the presence of air.

The zeolite has then been submitted to an ion exchange by refluxing it in an excess of 0.5N ammonium chloride during 4 hours.

After washing and drying, the powder was compressed, crushed and sieved.

This treated zeolite presents a bidimensional channel system comprising channels formed by 10-membered oxygen atom rings (4.3×5.5 Å) connected to channels formed by 8-membered oxygen atom rings (3.4×4.8 Å). The Si/Al atomic ratio of this zeolite was 5.

A sample of the zeolite was charged into a tubular reactor of the continuous flow type, for its use as catalyst.

The hydrogen form was obtained by calcining the catalyst in the reactor itself at a temperature of 673 K. under nitrogen during 1 hour.

(b) Use:

An aqueous ethanol solution derived from a fermentation liquid containing about 94% by weight of ethanol was used as feed.

This aqueous ethanol solution has been passed in the gaseous phase over the catalyst at a weight hourly space velocity (WHSV) of ethanol of 2.5 hours$^{-1}$, together with 5 moles of dry inert gas (diluent) per mole of ethanol. The contact time of the reagent with the catalyst was 0.6 second.

The reaction was carried out at atmospheric pressure.

The reaction products were analyzed on line by capillary gaseous chromatography (see table 1 below).

Example 2

Preparation of the hydrogen form of a ZEOLON 400 zeolite and use of this catalyst for converting ethanol into ethylene.
(a) Preparation:

The catalyst was prepared from a commercial zeolite: ZEOLON 400 (Norton, lot no. 43114).

X-ray analysis has shown that this product was clinoptilolite.

The typical unit cell composition of natural clinoptilolite is given by J. A. Breger et al (Am. Mineral, 55,825 (1970)):

$$X_2O; Al_2O_3; 10SiO_2; 3H_2O$$

X being predominantly K and Na, and to a minor extent Ca and Mg. The product was pretreated as described in example 1.

This zeolite presents four kinds of channels types extending in three different directions, i.e. channels with 10-membered rings (7.05×4.25 Å), 8-membered rings (4.60×3.95 Å), 8-membered rings (5.40×3.90 Å) and 8-membered rings (5.20×3.90 Å). The Si/Al atomic ratio was 5.
(b) Use:

The reaction conditions were the same as in example 1. The results of this test are given in table 1.

Example 3

Preparation of the hydrogen form of a zeolite chabazite and use of this catalyst for converting ethanol into ethylene.
(a) Preparation:

The catalyst was prepared from a natural zeolite: the chabazite of Bowie, Ariz., U.S.A.

The identification of this mineral was made by X-ray analysis.

The typical unit cell composition for chabazite is given by W. M. Meier and D. H. Olson ("Atlas of Zeolite Structure Types, p. 25):

$$Ca_6Al_{12}Si_{24}O_{72}.40H_2O$$

The zeolite was treated as described in example 1, except that the zeolite was not calcined at 823 K.

This zeolite presents a tridimensional system of channels with 8-membered rings (3.6×3.7 Å) and had a Si/Al atomic ratio of 2.
(b) Use:

The reaction conditions were the same as in example 1. The results are given in table 1.

Example 4

Preparation of the hydrogen form of a zeolite chabazite/erionite and use of this catalyst for converting ethanol into ethylene.
(a) Preparation:

The catalyst was prepared from a natural zeolite: the chabazite/erionite of Bowie, Ariz., U.S.A.

The identification of the mineral was done by X-ray analysis and disclosed the presence of a mixture of chabazite and erionite having each tridimensional channels with 8-membered rings.

The zeolite was treated as described in example 3.

The Si/Al ratio of the zeolite was 2-3.
(b) Use:

The reaction conditions were the same as in example 1. The results are given in table 1.

Example 5

Preparation of the hydrogen form of a zeolite erionite and use of this catalyst for converting ethanol into ethylene.
(a) Preparation:

The catalyst was prepared from a natural zeolite: erionite, Nevada, U.S.A.

X-ray analysis has shown that the product was the mineral erionite having a tridimensional channel system with 8-membered rings (3.6×5.2 Å).

For erionite, the following typical unit cell composition is given by W. M. Meier and D. H. Olson ("Atlas of Zeolite Structure Types", p. 35):

$$(Na_2, Ca\ldots)_{4.5}Al_9Si_{27}O_{72}.27H_2O$$

The zeolite was treated as described in example 3.

The Si/Al ratio of this zeolite was 3.
(b) Use:

The reaction conditions were the same as in example 1. The results are given in table 1.

The results obtained in examples 1 to 5 are given in table 1.

The table shows the activity and the carbon selectivity for ethylene for the various natural zeolites used in the dehydration of ethanol into ethylene.

For the results appearing in this table,
(1) The maximum theoretical conversion of ethanol into hydrocarbons and water is always reached and is respectively 61% and 39% by weight.
(2) The conversion percentage is expressed as follows:

$$\frac{\text{weight (in g) of ethanol converted}}{\text{weight (in g) of ethanol fed}} \times 100$$

(3) The carbon selectivity for ethylene (% by weight) is expressed as follows:

$$\frac{\text{weight (in g) of ethylene formed}}{\text{weight (in g) of hydrocarbons formed}} \times 100$$

The study of table 1 shows that, in all the examples under the reaction conditions mentioned, ethanol is completely converted and the carbon selectivity for ethylene is of 100% by weight, except for H-ZEOLON 700 for which the carbon selectivity is of 99.8% by weight.

TABLE 1

NATURAL ZEOLITE CATALYSTS

| CATALYSTS: | H-ZEOLON 700 | H-ZEOLON 400 | H-CHABAZITE | H-CHABAZITE/ERIONITE | H-ERIONITE |
|---|---|---|---|---|---|
| Example n° | 1 | 2 | 3 | 4 | 5 |
| Si/Al | 5 | 5 | 2 | 2-3 | 3 |
| Temperature (K) | 536 | 531 | 483 | 516 | 483 |
| WHSV (h$^{-1}$) | 2.5 | 2.5 | 2.5 | 2.5 | 2.5 |
| Contact time (sec) | 0.6 | 0.6 | 0.6 | 0.6 | 0.6 |
| Pressure (atm) | 1.0 | 1.0 | 1.0 | 1.0 | 1.0 |
| Test time: | | | | | |
| g ethanol/g catalyst | 10.0 | 60.0 | 60.0 | 60 | 60 |
| Conversion (%) | 100.0 | 100.0 | 100.0 | 100.0 | 100.0 |
| Selectivity for $C_2H_4$ (% by weight) | 99.8 | 100.0 | 100.0 | 100.0 | 100.0 |

Example 6

Stability test of the catalyst H-ZEOLON 700 of example 1.

The H-ZEOLON 700 catalyst was prepared from commercial zeolite ZEOLON 700 (Norton) as described in example 1.

A sample of this catalyst was treated respectively with 0.5N hydrochloric acid, with 0.1N sodium hydroxide and with 0.5N hydrochloric acid, each time at a temperature of 353 K. and during half an hour.

After each use, the catalyst was washed and air-dried. The X-ray analysis has shown that the zeolite structure was intact after this treatment. This zeolite had the same structure as this of example 1.

The operating conditions and the results are given in table 2.

This table shows that the catalyst H-ZEOLON 700 shows a rate of conversion of ethanol into ethylene of 100% and at the same time a carbon selectivity for ethylene of 100% by weight.

The table also shows the quick deactivation of the non treated H-ZEOLON 700 catalyst.

On the contrary, the treatments with an acid and a base considerably increase the stability of the same catalyst for selectively producing ethylene from aqueous ethanol (94% by weight) obtained by distilling a fermentation liquor.

TABLE 2

CATALYST: H-ZEOLON 700

| | NOT-TREATED | | | TREATED | | |
|---|---|---|---|---|---|---|
| REACTION CONDITIONS | | | | | | |
| Temperature (K) | 536 | 536 | 536 | 536 | 536 | 536 |
| WHSV (h$^{-1}$) | 2.5 | 2.5 | 2.5 | 2.5 | 2.5 | 2.5 |
| Contact time (sec) | 0.6 | 0.6 | 0.6 | 0.6 | 0.6 | 0.6 |
| Pressure (atm) | 1.0 | 1.0 | 1.0 | 1.0 | 1.0 | 1.0 |
| g ethanol/g catalyst | 10 | 25 | 60 | 10 | 25 | 60 |
| Conversion (%) | 100.0 | 55.5 | 36.9 | 100.0 | 100.0 | 100.0 |
| DISTRIBUTION OF THE PRODUCTS (% by weight) | | | | | | |
| Diethyl ether | 0.0 | 15.0 | 6.0 | 0.0 | 0.0 | 0.0 |
| Acetaldehyde | 0.0 | 0.0 | 0.0 | 0.0 | 0.0 | 0.0 |
| Water | 39.1 | 35.5 | 37.6 | 39.1 | 39.1 | 39.1 |
| Hydrocarbons | 60.9 | 49.5 | 56.4 | 60.9 | 60.9 | 60.9 |
| CO | 0.0 | 0.0 | 0.0 | 0.0 | 0.0 | 0.0 |
| $CO_2$ | 0.0 | 0.0 | 0.0 | 0.0 | 0.0 | 0.0 |
| DISTRIBUTION OF THE HYDROCARBONS | | | | | | |

TABLE 2-continued

CATALYST: H-ZEOLON 700

| | NOT-TREATED | | | TREATED | | |
|---|---|---|---|---|---|---|
| (% by weight) | | | | | | |
| Methane | 0.0 | 0.0 | 0.0 | 0.0 | 0.0 | 0.0 |
| Ethylene | 100.0 | 100.0 | 100.0 | 100.0 | 100.0 | 100.0 |
| Propylene | 0.0 | 0.0 | 0.0 | 0.0 | 0.0 | 0.0 |
| $C_3^+$ | 0.0 | 0.0 | 0.0 | 0.0 | 0.0 | 0.0 |

Example 7

Preparation of a H-Ferrierite catalyst (Si/Al=12) and conversion of ethanol into ethylene with this catalyst.

(a) Preparation:

This zeolite catalyst was synthesized by the procedure described in the example 9 of the patent EP 0.012.473.

The reaction mixture composition, on a molar base, was the following:

$$93.5SiO_2/4Al_2O_3/10Na_2O/17Na_2SO_4/$$

$$36.7 \text{ piperidine}/1938H_2O.$$

The solid product obtained was calcined at 823 K. during 24 hours and analyzed by X-ray diffraction. It was a ferrierite zeolite.

The zeolite was ion exchanged with an ammonium cation by refluxing the catalyst in an excess of 0.5N ammonium chloride during 4 hours.

The catalyst was then washed and dried.

The hydrogen form was obtained by calcining the catalyst in the reactor itself at a temperature of 673 K. under nitrogen during 1 hour.

Based on the atomic absorption results, the obtained crystalline catalyst had a Si/Al atomic ratio of 12. On the other hand, it had the same structure (channels with 10-membered rings and channels with 8-membered rings) as the zeolite of example 1.

(b) Use:

A sample of this catalyst was charged into a tubular reactor.

The reaction conditions were the same as described in example 1. The results of this test are given in table 3.

Example 8

Stability test of the H-Ferrierite catalyst of example 7.

A sample of the catalyst of example 7, charged into a tubular reactor of the continuous flow type and calcined at a temperature of 673 K., was submitted to a life test.

As feed, an aqueous ethanol solution resulting from a fermentation liquor and containing about 94% by weight of ethanol was used.

This solution was passed in the gaseous phase over the catalyst.

The operating conditions were the following:

| weight hourly space velocity | 2.5 h$^{-1}$ |
| contact time | 0.6 second |
| pressure | atmospheric |
| temperature | 536 K |
| test time | until 100 g of ethanol fed per g of catalyst. |

The ethanol was quantitatively converted into ethylene with an carbon selectivity for ethylene of 99.8% by weight.

The conversion rate of ethanol into ethylene and the selectivity for ethylene did not change in function of time.

This H-ferrierite catalyst has thus a remarkable stability for selectively producing ethylene from ethanol in the presence of water.

Example 9

Preparation of a H-T catalyst and conversion of ethanol into ethylene with this catalyst.

(a) Preparation:

A zeolite of the T type was prepared from the two following solutions:

solution 1:
57.0 g of SiO$_2$ (aerosil);
18.3 g of NaOH;
132.0 ml of water.

solution 2:
10.0 g of NaAlO$_2$;
10.3 g of KOH;
126.0 ml of water.

The solution 1 was added to the solution 2 under continuous stirring during 5 minutes.

The reaction mixture composition, on a molar basis, was the following:

20SiO$_2$; Al$_2$O$_3$; 6Na$_2$O; 310H$_2$O

The gel obtained was crystallized in autoclaves at a temperature of 373 K. without agitation during 7 days.

The obtained solid product was separated by filtration from the liquid supernatant solution, then washed with water and dried.

An ionic exchange with the ammonium cation was obtained by refluxing the catalyst in an excess of 0.5N ammonium chloride during 4 hours.

The hydrogen form of the catalyst was obtained by calcining the catalyst in the reactor itself at 623 K. under nitrogen during 1 hour.

The obtained catalyst had a Si/Al atomic ratio of 10.

The structure of this zeolite which is similar to that of erionite and offretite was characterized by the hydroconversion of n-decane (Martens J. A., Tielen M., Jacobs P. A. and Weitkamp J., Zeolites, 4, 95–107, 1984) and has shown a tridimensional channel system with 8-membered rings.

(b) Use:

A sample of this catalyst was charged into a tubular reactor.

The reaction conditions were the same as in example 1.

Example 10

Preparation of a H-ZSM-47 (ZSM-6) catalyst and conversion of ethanol into ethylene with this catalyst.

(a) Preparation:

The ZSM-47 (ZSM-6) zeolite was prepared from the three following solutions:

solution 1:
40.88 g of 40% colloidal silica (Ludox AS 40, Du Pont, U.S.A.);

solution 2:
6.15 g of tetramethylammonium chloride (TMACl);
6.15 ml of water.

solution 3:
1.967 g of NaAlO$_2$;
2.52 g of NaOH;
13.5 ml of water.

The three solutions were mixed under vigorous stirring during 15 minutes.

The obtained gel had the following molar composition:

28SiO$_2$/Al$_2$O$_3$/4Na$_2$O/6TMACl/260H$_2$O.

This gel was crystallized in autoclaves at a temperature of 453 K. without agitation during 7 days; the product was then washed, air-dried and air-calcined at a temperature of 823 K. during 12 hours.

The obtained zeolite was then ion-exchanged with ammonium cations by refluxing the catalyst in an excess of 0.5N ammonium chloride during 4 hours.

Before using it as catalyst, the zeolite was activated in the reactor itself by calcining it at 673 K. under nitrogen during 1 hour.

This catalyst had a Si/Al atomic ratio of 15. By the hydroconversion of n-decane, it has been shown that this zeolite has a channel system with 8 membered oxygen atom rings such as in erionite.

(b) Use:

A sample of this catalyst was charged in a tubular reactor.

The reaction conditions were the same as described in example 1.

The following table 3 shows the results obtained in the examples 7, 9 and 10.

This table shows, for the dehydration reaction of ethanol on synthetic zeolites, the reaction conditions, the rate of conversion and the carbon selectivity for ethylene.

It is obvious from this table that in the examples 7, 9 and 10 under the reaction conditions mentioned, a conversion rate of 100% and at the same time a carbon selectivity for ethylene of 100% by weight, except for the ferrierite which has a selectivity of 99.8% by weight, are obtained.

TABLE 3

| Synthetic zeolite catalyst. | | | |
| --- | --- | --- | --- |
| | CATALYSTS: | | |
| | H-FERRIERITE | H-T | H-ZSM-47 |
| Example n° | 7 | 9 | 10 |
| Si/Al | 12 | 10 | 15 |
| Temperature (K) | 536 | 512 | 625 |
| WHSV (h$^{-1}$) | 2.5 | 2.5 | 2.5 |
| Contact time (sec) | 0.6 | 0.6 | 0.6 |

TABLE 3-continued

Synthetic zeolite catalyst.

| | CATALYSTS: | | |
|---|---|---|---|
| | H-FERRIERITE | H-T | H-ZSM-47 |
| Pressure (atm) | 1.0 | 1.0 | 1.0 |
| Test time: | | | |
| g ethanol/g catalyst | 1000 | 40 | 60 |
| Conversion (%) | 100.0 | 100.0 | 100.0 |
| Selectivity for $C_2H_4$ (% by weight) | 99.8 | 100.0 | 100.0 |

Example 11

Preparation of a H-Ferrierite catalyst and conversion of ethanol into ethylene with this catalyst.
(a) Preparation This catalyst of the zeolite type was synthesized by the process described in example 8 of the European patent EP 0.012.473.

The reaction mixture composition, on a molar basis, was the following:

$$93.5 SiO_2/2Al_2O_3/17.7Na_2O/$$

$$9.3Na_2SO_4/36.7 \text{ piperidine}/1938H_2O.$$

The solid product was calcined at 823 K. during 24 hours and analyzed by X-ray diffraction. It was a ferrierite zeolite having the same structure as that of the example 1.

The hydrogen form of the catalyst was obtained as described in example 8.

On the basis of the atomic absorption results, the obtained crystalline catalyst had a Si/Al atomic ratio of 23.

(b) Use:

A sample of this catalyst was charged in a tubular reactor.

The reaction conditions were the same as in example 1.

The following table 4 shows the reaction conditions and the results.

These tests have shown that there are no reaction conditions for which the conversion rate is of about 100% and the selectivity for ethylene is greater than 99% by weight.

It has to be noted that the Si/Al atomic ratio is greater than the claimed maximum: Si/Al=20.

Thus, although the zeolite has a structure formed by 10-membered rings linked to channels formed by 8-membered rings and meets the first critical parameter, it does not give the desired results, since the second parameter (Si/Al atomic ratio) is greater than the claimed maximum.

TABLE 4

CATALYST: H-FERRIERITE

| REACTION CONDITIONS | | |
|---|---|---|
| Temperature (K) | 490 | 520 |
| WHSV ($h^{-1}$) | 2.5 | 2.5 |
| Contact time (sec) | 0.6 | 0.6 |
| Pressure (atm) | 1.0 | 1.0 |
| Conversion (%) | 86.3 | 100.0 |
| DISTRIBUTION OF THE PRODUCTS (% by weight) | | |
| Diethyl ether | 13.9 | 0.0 |
| Acetaldehyde | 0.0 | 0.0 |
| Water | 35.7 | 39.1 |
| Hydrocarbons | 50.4 | 60.9 |
| CO | 0.0 | 0.0 |
| $CO_2$ | 0.0 | 0.0 |

TABLE 4-continued

CATALYST: H-FERRIERITE

| DISTRIBUTION OF THE HYDROCARBONS (% by weight) | | |
|---|---|---|
| Methane | 0.0 | 0.0 |
| Ethylene | 99.4 | 78.9 |
| Ethane | 0.0 | 0.0 |
| Propylene + propane | 0.0 | 3.3 |
| $C_3^+$ | 0.6 | 17.8 |

Example 12

Preparation of a H-ZSM-22 catalyst and conversion of ethanol into ethylene with this catalyst.
(a) Preparation:

A zeolite of the crystalline ZSM-22 type was prepared from the two following solutions:
Solution 1:
  72 g of 40% colloidal silica (Ludox AS-40, Du Pont, U.S.A.);
  124 ml of water;
Solution 2:
  3.54 g of $Al_2(SO_4)_3.18H_2O$;
  7.75 g of KOH;
  16.7 g of 1,6-diaminohexane;
  177 ml of water.

The solution 1 was added to the solution 2 under vigourous stirring.

The composition of the gel obtained, on a molar basis, was the following:

$$90SiO_2/Al_2O_3/13K_2O/0.27$$
$$1,6\text{-diaminohexane}/3620H_2O$$

The mixture was heated in autoclaves at 433 K. under stirring during 2 days.

After washing, drying and calcining in air at a temperature of 823 K. during 24 hours, the solid product was analyzed by X-ray diffraction. The analysis revealed the presence of a high crystalline phase of ZSM-22.

In order to obtain the hydrogen form, the zeolite was ion exchanged at 353 K. with 0.5N hydrochloric acid, using a liquid/solid ratio of 50 and stirring it during one hour.

Before using it as catalyst, the zeolite was activated in the reactor itself by calcining it at 673 K. under nitrogen during 1 hour.

The crystalline catalyst had a Si/Al atomic ratio of 45 on the basis of the results of the atomic absorption analysis, while its structure was characterized by an unidirectional and monodimensional linear channel system with 10-membered rings having apertures of 5.5×4.5 Å (Kokotailo G. T., Schlenker J. L., Dwyer F. G., Valyocsik E. W., Zeolites, 5, 349–351, 1985).

(b) Use:

The reaction conditions were the same as in example 1.

The reaction conditions and results are given in table 5.

These tests have shown that it was not possible to reach a quantitative conversion rate of ethanol and at the same time a carbon selectivity for ethylene of about 100% when this H-ZSM-22 zeolite having a Si/Al atomic ratio of 45 (a ratio which is greater than the claimed maximum) is used.

TABLE 5

CATALYST: H-ZSM-22

REACTION CONDITIONS

| | | |
|---|---|---|
| Temperature (K) | 512 | 526 |
| WHSV ($h^{-1}$) | 2.5 | 2.5 |
| Contact time (sec) | 0.6 | 0.6 |
| Pressure (atm) | 1.0 | 1.0 |
| Conversion (%) | 97.2 | 100.0 |

DISTRIBUTION OF THE PRODUCTS (% by weight)

| | | |
|---|---|---|
| Diethyl ether | 0.4 | 0.0 |
| Acetaldehyde | 0.0 | 0.0 |
| Water | 39.0 | 39.1 |
| Hydrocarbons | 60.6 | 60.9 |
| CO | 0.0 | 0.0 |
| $CO_2$ | 0.0 | 0.0 |

DISTRIBUTION OF THE HYDROCARBONS (% by weight)

| | | |
|---|---|---|
| Methane | 0.0 | 0.0 |
| Ethylene | 99.7 | 96.5 |
| Ethane | 0.0 | 0.0 |
| Propylene + propane | 0.0 | 0.2 |
| $C_3^+$ | 0.3 | 3.3 |

Example 13

Preparation of a hydrogen form of a L zeolite and use of this catalyst for converting ethanol into ethylene.

(a) Preparation:

The catalyst was prepared from a commercial zeolite: Linde SK-45 type (Union Carbide, U.S.A., lot no. 12508-86).

The typical unit cell composition of the Linde L type zeolite is given by W. M. Meier and D. H. Olson ("Atlas of Zeolite Structure Type", p. 59):

$$K_6Na_3Al_9Si_{27}O_{27}.21H_5O.$$

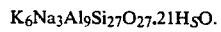

The zeolite was ion-exchanged with the ammonium cation.

The ion-exchange was effected five times by refluxing the catalyst in an excess of 0.5N ammonium chloride during 4 hours.

After washing and drying, the obtained powder was compressed, crushed and sieved.

In order to use it as catalyst, a sample of the zeolite was charged into a tubular reactor of the continuous flow type.

The hydrogen form was obtained by calcining the catalyst in the reactor itself at a temperature of 673 K. under nitrogen during 1 hour.

(b) Use:

The reaction conditions were the same as in example 1. Table 6 shows the reaction conditions and the obtained results.

The H-L zeolite is able to catalyze selectively the dehydration reaction of ethanol into ethylene so as to obtain a quantitative conversion rate and at the same time a carbon selectivity for ethylene of 100% by weight at a temperature of 508 K. under the mentioned reaction conditions.

Table 6 shows however the quick deactivation or instability of the H-L catalyst: after feeding 25 g of ethanol per g of catalyst, the conversion has already diminished by more than 10%.

Although the Si/Al atomic ratio of this zeolite is 3, its structure is characterized by a monodimensional channel system with 12-membered rings (7.1 Å). This catalyst does not meet the two critical parameters of the present invention.

TABLE 6

CATALYST: H-L

REACTION CONDITIONS

| | | | | |
|---|---|---|---|---|
| Temperature (K) | 508 | 508 | 508 | 508 |
| WHSV ($h^{-1}$) | 2.5 | 2.5 | 2.5 | 2.5 |
| Contact time (sec) | 0.6 | 0.6 | 0.6 | 0.6 |
| Pressure (atm) | 1.0 | 1.0 | 1.0 | 1.0 |
| g ethanol/g catalyst | 5 | 15 | 25 | 30 |
| Conversion (%) | 100.0 | 97.9 | 89.9 | 85.1 |

DISTRIBUTION OF THE PRODUCTS (% by weight)

| | | | | |
|---|---|---|---|---|
| Diethyl ether | 0.0 | 1.3 | 6.1 | 8.7 |
| Acetaldehyde | 0.0 | 0.0 | 0.0 | 0.0 |
| Water | 39.1 | 38.8 | 37.6 | 37.0 |
| Hydrocarbons | 60.9 | 59.9 | 56.3 | 54.3 |
| CO | 0.0 | 0.0 | 0.0 | 0.0 |
| $CO_2$ | 0.0 | 0.0 | 0.0 | 0.0 |

DISTRIBUTION OF THE HYDROCARBONS (% by weight)

| | | | | |
|---|---|---|---|---|
| Methane | 0.0 | 0.0 | 0.0 | 0.0 |
| Ethylene | 100.0 | 100.0 | 100.0 | 100.0 |
| Ethane | 0.0 | 0.0 | 0.0 | 0.0 |
| Propylene + Propane | 0.0 | 0.0 | 0.0 | 0.0 |
| $C_3^+$ | 0.0 | 0.0 | 0.0 | 0.0 |

Example 14

Use of a H-ZEOLON 100 zeolite for converting ethanol into ethylene.

The commercial catalyst H-ZEOLON 100 (Norton, U.S.A., lot no. 82 113) was used.

X-ray analysis has shown that the zeolite was mordenite.

The typical unit cell composition for mordenite is given by W. M. Meier and D. H. Olson ("Atlas of Zeolites Structure Type", p. 69):

$$Na_8Al_8Si_{40}O_{96}.24H_2).$$

The powder was compressed, crushed and sieved.

In order to use it as catalyst, a sample of zeolite was charged into a tubular reactor of the continuous flow type.

The zeolite was activated in the reactor itself by a pretreatment at 673 K. under nitrogen during 1 hour.

The reaction conditions were the same as in example 1.

The reaction conditions and the results are set forth in the following table 7.

The table 7 shows that this H-ZEOLON 100 catalyst is able to catalyze selectively the dehydration reaction of ethanol into ethylene in order to obtain a quantitative conversion rate and at the same time a carbon selectivity for ethylene of 100% by weight at a temperature of 495 K. under the mentioned reaction conditions.

The table shows however the quick deactivation of the H-ZEOLON 100 catalyst

It has to be noted that the structure of the mordenite is essentially bidimensional, the main channels being formed by 12-membered rings (6.7×7.0 Å) linked through channels formed by 8-membered rings (2.9×5.7 Å).

The Si/Al atomic ratio is however 5.

This zeolite does not meet the two critical parameters of the catalyst selected according to the present invention.

TABLE 7

| | | | | | | |
|---|---|---|---|---|---|---|
| CATALYST: H-ZEOLON 100 | | | | | | |
| REACTION CONDITIONS | | | | | | |
| Temperature (K) | 495 | 495 | 495 | 495 | 495 | 495 |
| WHSV ($h^{-1}$) | 2.5 | 2.5 | 2.5 | 2.5 | 2.5 | 2.5 |
| Contact time (sec) | 0.6 | 0.6 | 0.6 | 0.6 | 0.6 | 0.6 |
| Pressure (atm) | 1.0 | 1.0 | 1.0 | 1.0 | 1.0 | 1.0 |
| g ethanol/g catalyst | 12 | 22 | 27 | 32 | 42 | 62 |
| Conversion (%) | 100.0 | 98.4 | 85.5 | 54.6 | 25.4 | 15.3 |
| DISTRIBUTION OF THE PRODUCTS (% by weight) | | | | | | |
| Diethyl ether | 0.0 | 1.4 | 3.9 | 3.8 | 2.8 | 2.8 |
| Acetaldehyde | 0.0 | 0.0 | 0.0 | 0.0 | 0.0 | 0.0 |
| Water | 39.1 | 38.8 | 38.2 | 38.2 | 38.4 | 38.4 |
| Hydrocarbons | 60.9 | 59.8 | 57.9 | 58.0 | 58.8 | 58.8 |
| CO | 0.0 | 0.0 | 0.0 | 0.0 | 0.0 | 0.0 |
| $CO_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 100.0 | 100.0 | 100.0 | 100.0 | 100.0 | 100.0 |
| Ethane | 0.0 | 0.0 | 0.0 | 0.0 | 0.0 | 0.0 |
| Propylene + Propane | 0.0 | 0.0 | 0.0 | 0.0 | 0.0 | 0.0 |
| $C_3^+$ | 0.0 | 0.0 | 0.0 | 0.0 | 0.0 | 0.0 |

What we claim is:

1. A process for obtaining ethylene from anhydrous or aqueous ethanol by means of a catalyst of the crystalline aluminosilicate zeolite type of natural or synthetic origin, in which at least one catalyst of the crystalline zeolite type is used, said catalyst having, on the one hand, channels or pores formed by cycles or rings of oxygen atoms having 8 and/or 10 elements or members and, on the other hand, an atomic Si/Al ratio of less than about 20, this catalyst being used under such temperature conditions that it has a carbon selectivity for ethylene of about 100% by weight and has a rate of conversion of about 100% of ethanol into ethylene.

2. A process according to claim 1, in which at least one natural zeolite selected from the group consisting of ferrierite, heulandite, clinoptilolite, stilbite, erionite, chabazite levinyte and mixtures thereof.

3. A process according to claim 1, in which at least one synthetic catalyst selected from the group consisting of the ZSM-47 ZSM-6, T, ZSM-22 zeolites, synthetic ferrierite, chabazite, erionite and clinoptilolite, is used.

4. A process according to claim 2, in which the zeolite catalyst is previously submitted to an ion exchange and/or to a treatment at a high temperature or to a treatment by means of an acid or a base or to a combination of these treatments.

5. A process according to claim 3, in which the zeolite catalyst is previously submitted to an ion exchange and/or to a treatment at a high temperature or to a treatment by means of an acid or a base or to a combination of these treatments.

6. A process according to claim 2, in which the catalyst is used under the hydrogen form.

7. A process according to claim 3, in which the catalyst is used under the hydrogen form.

8. A process according to claim 1, in which aqueous ethanol containing at least 4% by weight of ethanol is used.

9. A process according to claim 8, in which an ethanol solution resulting from a biomass fermentation or synthesized from coal or petroleum synthesized syngas is used.

* * * * *